United States Patent [19]

Lee

[11] Patent Number: 4,556,387

[45] Date of Patent: Dec. 3, 1985

[54] DENTAL ARTICULATOR

[76] Inventor: Robert L. Lee, 22937 Grand Terrace Rd., Colton, Calif. 92324

[21] Appl. No.: 611,342

[22] Filed: May 17, 1984

[51] Int. Cl.$^4$ ............................................. A61C 11/00
[52] U.S. Cl. ..................................................... 433/58
[58] Field of Search ....................... 433/57, 58, 59, 60, 433/61, 62, 63, 64, 65

[56] References Cited

U.S. PATENT DOCUMENTS 2,235,524  3/1941  Lentz ..................................... 433/58

FOREIGN PATENT DOCUMENTS 413257  7/1924  Fed. Rep. of Germany ........ 433/60

Primary Examiner—Robert Peshock
Attorney, Agent, or Firm—Knobbe, Martens, Olson & Bear

[57] ABSTRACT

A dental articulator is disclosed, having a lower frame with a pair of condyles thereon defining a hinge axis, an upper frame carrying a pair of guides for slideably and pivotally receiving the condyles to permit the relative positions of the upper and lower frames to simulate movements of the human jaw, and retainers outboard of the condyles on opposite sides of the articulator connecting the upper frame to the lower frame and urging the upper and lower frames into a centric relationship while permitting the frames to be moved to simulate human jaw movements. The retainers are preferably pivotally joined to the upper frames on the hinge axis and may be loops of elastomeric material. A sleeve may be provided on each retainer so that a loop of the retainer protrudes from each end of the sleeve. The sleeve and retainer function as a hinge when pivoting the articulator to a fully opened position. An incisal pin is provided at the front of the articulator extending downwardly from the upper frame and supported by the lower frame. A forward-extending horizontal guide rod is provided along side the incisal pin for locating the upper and lower frames in a non-centric relationship.

12 Claims, 3 Drawing Figures

U.S. Patent    Dec. 3, 1985    4,556,387
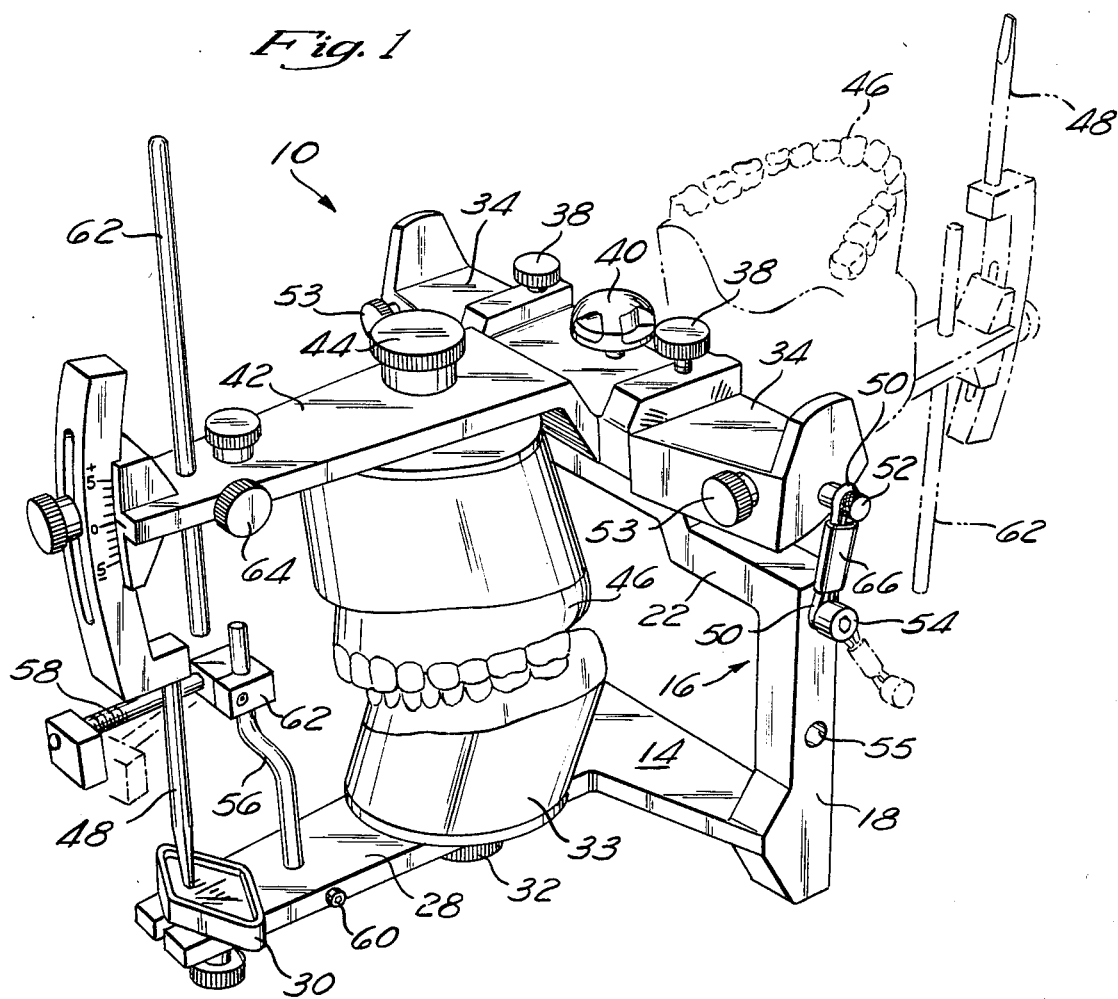
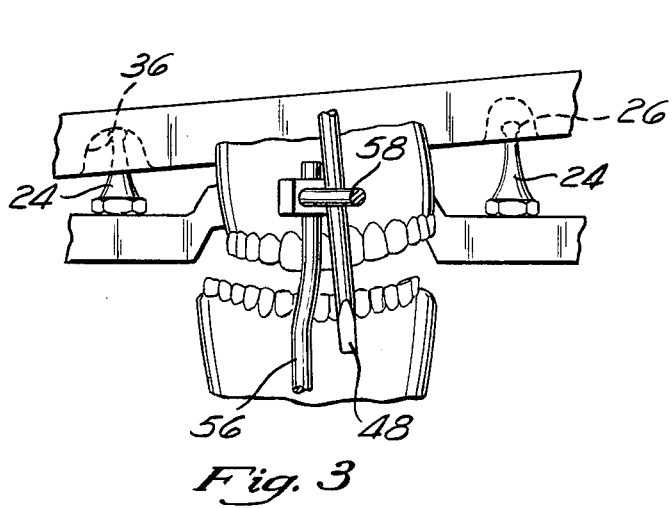
Fig. 3
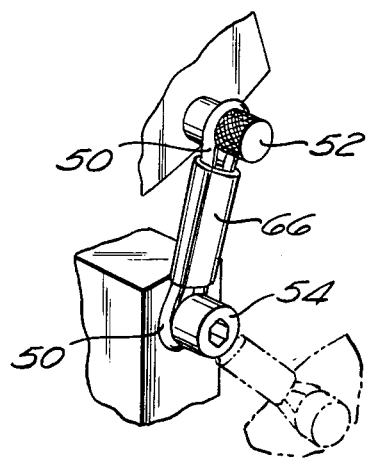
Fig. 2

DENTAL ARTICULATOR

BACKGROUND OF THE INVENTION

This invention relates to dental articulators, and specifically to articulators for use in modeling or simulating the movement of the human jaw.

Dental articulators are used in prosthodontics. The field of fixed prosthodontics generally relates to nonremovable replacements or substitutes for natural teeth, such as bridges and caps. The field of removable prosthodontics includes removable dentures. Dental articulators are used in both fields in making dental prosthesis. One important characteristic of a dental articulator is the ability to closely simulate the actual centric, lateral, and protrusive jaw movements of the patient in order that the prosthodontist may produce a comfortable and effective dental prosthesis.

Several different types of dental articulators are known. One common type of articulator is the axle and track articulator manufactured by Hanau Engineering Company. An axle and track articulator has an upper frame and a lower frame. Slots or tracks on the lower frame carry an axle attached to the upper frame. See, e.g., U.S. Pat. No. 1,733,507 to McCollun. Although axle and track articulators do only a fair job of simulating human jaw movements, they remain in widespread use today because of their simplicity, smoothness of operation, and convenience. Such articulators may be opened fully without separation by simply pivoting the upper frame 180° on the axle.

A second type of articulator is the articulator-condyle, or "arcon" type. Arcon articulators are characterized by a lower frame carrying a pair of condyle balls and an upper frame having guides which receive the condyles and permit the upper frame to pivot and slide on the condyles and more closely simulate human jaw movement. Such arcon articulators are exemplified by U.S. Pat. No. 3,590,487. Major advances have been made in arcon articulator technology to the extent that a patient's jaw movements can now be almost precisely duplicated. See, e.g., U.S. Pat. Nos. 3,452,439; 3,694,919; 3,896,550; 4,034,474; 4,034,475; and 4,209,909, all to Robert L. Lee.

Despite the superiority of arcon articulators in simulating human jaw movement, they have, nevertheless, failed to supplant the Hanau-type axle and track articulators, for several reasons. One of the advantages of an axle and track articulator is that the frames stay together for hinging and tracking movements and they may be opened 180° so that the prosthodontist may work on the tooth models for both the upper and lower jaw from above. By contrast, in most arcon-type articulators, the frames can be separated at any time and condyles completely leave the guide blocks and articulators come apart when the frames are opened more than about 80° to 90°.

In the field of removable prosthodontics, manufactured teeth are positioned in a wax base on the articulator. It is common, when using an arcon articulator, for the teeth to lift the guides slightly above the condyles, introducing inaccuracies into the prosthodontic process. The use of springs to bias the guides onto the condyles has been unsatisfactory, because the required spring pressure hinders opening of the articulator.

It is important that the prosthodontist be able to readily and positively align the upper and lower frames of the articulator in the centric position. (The centric position is that position corresponding to a fully retracted and centered lower jaw.) It is also desirable that the articulator return to the centric position of its own accord, except when study of a particular non-centric position is desired, in which case the prosthodontist should be able to either hold that non-centric position or repeatably return the articulator to that position as necessary. At the same time, it is desirable that the articulator be easily opened and closed while maintaining the centric position.

For many of the reasons discussed above, approximately 50% of all dental schools in the United States require dental students to purchase two different articulators: an arcon-type articulator for fixed prosthodontics, and an axle and track articulator for removable prosthodontics.

Some efforts have been made in the prior art to spring-bias articulators into a desired position. An early example is Burch, U.S. Pat. No. 1,080,809. This patent discloses the use of a spring on an axle and slot articulator to bias the articulator into an open centric position.

Various methods have been used in the past to bias arcon-type articulators into centric position and prevent unwanted separation of the condyles from the guides. One such method is a coil spring connecting the upper frame to the lower frame between the condyles. This arrangement has proved unsatisfactory because the spring is extended when the articulator is opened and prevents full opening of the articulator. Moreover, the spring biases the articulator closed, hindering study of hinging motion. Additionally, the spring is bent if the articulator is opened too far. Rubber bands placed between the upper and lower frames between the condyles present similar disadvantages.

Accordingly, an object of the present invention is to provide a means for biasing an articulator into the centric position while permitting free opening and closing of the articulator in that position.

Another object of the present invention is to provide a novel hinge on which an arcon-type articulator can pivot into a fully opened position of at least 180°. Another object is to maintain the guide means in contact with condyle during eccentric movements.

Yet another object of the present invention is to provide a means for holding the articulator in a non-centric position and for repeatably reproducing desired non-centric positions of the articulator.

BRIEF DESCRIPTION OF THE INVENTION

In furtherance of the foregoing objects, there is provided in connection with the present invention an arcon-type dental articulator, comprising a lower frame having a pair of condyles thereon defining a hinge axis and an upper frame carrying a pair of guide blocks having openings for receiving the condyles. The guide blocks slidably and pivotally receive the condyles to permit the relative positions of the upper and lower frames to simulate the human jaw in a centric position and to simulate side shift and protrusive human jaw movements. Retainers are provided on opposite sides of the articulator connecting the upper frame to the lower frame so that the condyles are between the retainers. The retainers urge the upper and lower frames into a centric relationship.

The retainers preferably intersect the hinge axis, and, most preferably, are at least in part concentric with the hinge axis when the upper and lower frames are in centric relationship.

In accordance with another aspect of the present invention, the retainers are loops of elastomeric material having a generally circular cross-section. The retainers preferably have a sleeve thereon or are otherwise constructed so that a loop of retainer extends from each end of the sleeve and the sleeve separates or spaces the upper frame from the lower frame and functions as a hinge connecting the upper and lower frames about which the frames can pivot to a fully opened 180° position after the condyles separate from the guide blocks. The sleeve also maintains the retainers on the upper and lower frames.

In still another embodiment of the present invention, there are provided coaxial pins inserted into the upper frame to which the retainers are attached. These pins lie along the hinge axis when the upper and lower frames are in centric relationship so that the retainers offer no elastic resistance to pivotal motion between the upper and lower frames when the frames are in centric relationship, but the retainers offer elastic resistance to side shift and protrusive movement of the frames.

In accordance with still another aspect of the present invention, the articulator has an arrangement for repeatedly reproducing eccentric movements. In a preferred approach, the articulator has an incisal pin mounted on the upper frame extending generally vertical downward which is supported by the lower frame when the frames are in a fully closed position. The incisal pin may also extend above the upper frame to support the upper frame in the fully open position. A generally horizontal incisal locator rod or eccentric positioner is supported by the lower frame and is laterally moveable into and out of contact with the incisal pin for locating the upper and lower frames in a non-centric relationship. The eccentric positioner may be moved into contact with the incisal pin to hold the frames in a desired non-centric position. The positioner may also be used as a marker by setting the rod in a desired position and then moving the incisal pin into and out of contact with the rod to repeatedly reproduce a particular non-centric position. The locator rod is preferably provided with indicia for indicating the relative positions of the locator rod and the incisal pin.

BRIEF DESCRIPTION OF THE DRAWINGS

FIG. 1 is a perspective view of the dental articulator of the present invention.

FIG. 2 is a close-up perspective of the retainer attached to the articulator.

FIG. 3 is a partial front elevation showing the use of the locator rod in conjunction with the incisal pin.

DETAILED DESCRIPTION OF THE PREFERRED EMBODIMENT

As seen in FIG. 1, the articulator 10 is an arcon-type articulator of the same general type as is disclosed in U.S. Pat. No. 4,209,909, to Robert L. Lee, the disclosure of which is hereby incorporated by reference. The articulator 10 has an upper frame 12 and a lower frame 14. Both the upper frame 12 and the lower frame 14 are generally T-shaped. The lower frame 14 also has a closed loop vertical frame member 16 having two vertical posts 18 joined at their upper end by a lateral truss 22. The lateral truss, at either end, carries a pair of styluses or condyles 24.

As is best seen in FIG. 3, the condyles are vertically-extending posts with generally spherical elements 26 on the upper end.

Referring again to FIG. 1, the lower frame 14 has a forward arm 28 supporting an incisal pin rest pad 30 at the forward end thereof. The forward arm 28 also has a mounting screw 32 to which any desired dental model 33 of the lower teeth of a patient may be mounted.

The upper frame 12 is provided with a pair of guide blocks 34 on either side of the rear portion of the articulator upper frame 12. The guide blocks are provided with a recessed guide surface 36, shown in phantom in FIG. 3. The recessed guide surface 36 pivotally and slidably receives the condyles 24 so that the upper frame 12 can pivot on the condyles 24 on a hinge axis extending through the two spherical elements 26. The guide blocks 34 are selected and positioned to model the jaw movement of the particular patient, and may be removed from the upper frame 12. A pair of guide block adjustment screws 38 may be loosened to permit the guide blocks 34 to be adjusted to a desired position by pivoting them generally about the hinge axis.

As is disclosed in U.S. Pat. No. 4,209,909, the guide surfaces 36 in the guide blocks 34 engage the condyles 24 to permit sliding and pivoting movement that mimics or simulates the movement of the human jaw. Accordingly, the guide blocks, together with the upper frame 12, may slide forward and back, side to side, and may pivot on the condyles. Generally, the most deeply recessed portion of the guide surfaces 36 corresponds to the centric position; i.e., the position of the human jaws in which the lower jaw is fully retracted and centered. By sliding the guide blocks 34 rearwardly on the condyles 24, protrusive movement of the human jaw is simulated. Lateral movement of the upper frame in relation to the lower frame simulates lateral side shift and lateral twisting movement of the human jaw.

The upper frame 12 may advantageously be provided with a centric pin 40. When depressed, the centric pin 40 enters a slot (not shown) on the lateral truss 22 and holds the articulator in the centric position.

An upper forward arm 42 on the upper frame 12 is juxtaposed over the lower forward arm 28 on the lower frame 14. The upper forward arm 42 extends forward from between the guide blocks 34. An upper mounting screw 44 on the upper forward arm 42 is provided for mounting an upper dental model 46.

An incisal rest pin 48 is attached to the front end of the upper forward arm 42 and extends generally vertically downward (when the articulator is in fully closed position) to the rest pad 30. Indicia are provided on both the incisal pin 48 and the rest pad 30 for indicating the height and transverse position of the incisal pin 48.

In accordance with the invention, a retainer 50 is provided laterally outboard of the condyles connecting the upper frame to the lower frame. The retainer 50 biases the upper frame toward the lower frame. Any elastic material suitable for performing this function may be used. Examples of suitable materials are metals (in the form of a spring) and elastomeric materials, such as butyl rubber, neoprene rubber, polyurethane, vulcanized natural rubber, nitrile rubber, polysulfide rubber, styrenebutadiene copolymer, isoprene rubber, and silicone rubber. Neoprene rubber having a circular cross-section and formed into a loop is particularly preferred.

In a preferred embodiment, an upper pin 52 is provided on each side of the upper frame 12 on the outward side of the guide blocks 34. It is preferred that the upper pins 52 be coaxial with the hinge axis through the condyles 24 when the articulator is in centric position. The upper pins 52 are held in place with locking screws 53.

A horizontal lower pin 54 is provided on the vertical post 18 of the lower frame 14 preferably directly below the upper pin 52. The retainer 50 extends from the upper pin 52 to the lower pin 54 providing a downward force, biasing the articulator 10 into the centric position. Although the retainer 50 and the pins 52 and 54 are visible in FIG. 1 only on one side of the articulator, these same elements are also provided on the opposite side of the articulator so that the condyles are generally between the retainers 50.

If separation of the upper frame 12 from the lower frame 14 is desired, the locking screws 53 are loosened and the upper pins 53 are removed from the upper frame 12. The upper frame 12 can then be lifted off the lower frame 14. For convenience, the upper pin 52 may be inserted in a storage hole 55 on the vertical post 18 when removed from the upper frame 12.

Of course, there are a number additional of ways of connecting the upper frame 12 to the lower frame 14 with a retainer 50. Other suitable structures, such as hooks, screws, notches, or appropriate protuberances or recesses may be provided on the upper frame 12 and the lower frame 14 for holding the ends of the retainer 50.

An eccentric positioner or locator pin 56 is provided on the forward arm 28 of the lower frame 14. The locator pin 56 extends generally vertically upward from the forward arm 28. Attached to the locator pin 56 and extending generally horizontally forward therefrom is an eccentric positioner or rod 58. The eccentric positioner rod 58 may be moved into contact with the incisal pin 48 by pivoting the rod 58 around the pin 56, or by pivoting the pin 56. In a preferred embodiment, the locator pin 56 is inserted into a hole in the forward arm 28 and is secured in place with a set screw 60. Likewise, a set screw 62 may be used to secure the locator rod to the locator pin.

It is preferred that the locator rod 58 be offset from the center of the articulator 10 by the radius of the incisal pin 48 so that the incisal pin 48 may slide against the locator rod 58 during protrusive movement. Indicia on the locator rod 58 indicate the extent of protrusive displacement from the centric position.

The dental articulator 10 of the present invention has the significant advantage that it may be fully opened. In other words, the upper frame may pivot from the fully closed position illustrated in solid figure in FIG. 1 through approximately 180° to the fully opened position shown in phantom. In the fully opened position, the upper frame is supported by the retainers 50 and by a support rod 62 extending generally vertically through the upper forward arm 42 of the upper frame. The support rod 62 may be a part of the incisal pin 48, or may be a separate structure as shown. An adjustment screw 64 is tightened against the support rod 62 to maintain it in position and to permit vertical adjustment of the support rod.

In pivoting the upper frame from the fully closed to the fully opened position, the upper frame pivots through about 80° on the hinge axis through the spherical elements 26 of the condyles 24. As the angle between the upper frame 12 and the lower frame 14 approaches 70° or 80°, the condyles begin to leave the guide blocks 34. The upper frame continues to pivot through the remainder of 180° with the retainers 50 serving as hinges. In the fully opened position, the guide blocks 34 of the upper frame 12 are supported by the retainers 50 as shown in phantom in FIG. 2.

With regard to the pivoting motion of the upper frame 12, it is important to note that the retainer 50 has been so situated as to provide no elastomeric resistance to pivoting motion throughout its movement. At the same time during the initial 0° to 80° to 90° of opening motion the retainer provides a strong force to bias the frames into engagement, and more particularly, into centric position. This is made possible by locating the retainer 50 on or around the hinge axis by placing the upper pins 52 in coaxial relationship on the hinge axis extending through the condyles 24 when the articulator is in the centric position.

Thus, unlike other arcon articulators, the articulator of the present invention is continually biased into a centric position by the retainers 50 during the jaw simulator movement, and yet can freely pivot from a fully closed to a fully opened position. Pivotal motion is facilitated by making the retainer 50 circular in cross-section so that the pin 52 may freely rotate in the retainer 50. Such rotation may be enhanced by lubricating the retainer 50 or forming the retainer 50 of a self-lubricating material. To obtain this movement, it is not essential that the retainer 50 be located laterally outboard of the condyles, so long as it may pivot about the hinge axis to avoid elastic resistance to opening and closing motion. It is important to note, however, that placement of the retainer 50 laterally outboard of the condyles 24 presents significant advantages. One such advantage is in leverage: a retainer outboard of the condyles can retain the condyles in the guides much more effectively and positively than can a retainer between the condyles. In addition, a pair of outboard retainers is more certain to deliver a balanced biasing force and functions more effectively as a hinge.

Another significant advantage of the present invention over prior art articulators may be realized by providing a stiff tubular sleeve 66 on the retainer 50 and forming the retainer 50 into a loop. Thus, as is most clearly illustrated in FIG. 2, the sleeve 66 is placed on the retainer 50 so that a loop of retainer 50 extends from either end of sleeve 66. The sleeve 66 has two important functions. First, it forms a relatively small loop in each end of the retainer 50, thus facilitating retention of the retainer 50 on the pins 52 and 54. In addition, the sleeve 66 provides the retainer 50 with rigidity. This rigidity contributes significantly to the efficacy of the retainer 50 as a hinge when pivoting the upper frame 12 to the fully opened position. It also serves as a separator by maintaining separation between the upper frame 12 and the lower frame 14 during such pivoting motion, providing smooth pivoting motion and preventing bothersome and potentially damaging contact between the two frame pieces. The sleeve 66 may be made of any material having sufficient rigidity to maintain separation between the upper frame 12 and the lower frame 14 during pivoting motion. Suitable materials include metal and plastic, and preferably resilient plastic or rubber tubing. Of course, the sleeve could be an integral part of the retainer itself.

Not only does the present invention facilitate the study of dental models in the centric position, it also permits accurate and repeatable location and maintenance of whatever non-centric position the prosthodontist desires to study. This is done, as illustrated in FIG. 3, through use of the eccentric positioner 58. In FIG. 3, the positioner or locator rod 58 is holding the incisal pin 48 to maintain the articulator 10 in a non-centric position. The condyle on the right in FIG. 3 has not left the guide surface 36. Rather, as is explained in U.S. Pat. No. 4,209,909, the guide surface 36 slopes so that the spacing between the frames 12 and 14 increases when the condyle 24 moves out of the centric position of the guide surface. In addition, the spacing between the dental models in FIG. 3 is exaggerated; in ordinary use, the teeth would be in contact.

In a preferred embodiment, the set screws 60 and 62 are tightened sufficiently to retain the eccentric locator or positioner rod 58 in any desired position against the centering pressure of retainers 50 and yet permit an operator to pivot the locator rod 58 (as shown in phantom in FIG. 1) to a new position without loosening the set screws 60 and 62. It is further preferred that the locator pin 56 be offset or bent away from the dental models 33 and 46 to permit a greater range of movement and positions for locator rod 58 and also to provide adequate clearance for the prosthodontist to work on the dental models.

The locator rod 58 may also be used as a reference for repeatable non-centric position of the articulator. Indicia provided on the locator rod 58 can be used to indicate the extent of protrusive movement. In addition, other non-centric movements may be accurately repeated by positioning the locator rod and then moving the articulator until the incisal pin 48 contacts the locator rod 58. It should also be noted that proper positioning of the locator rod alongside the guide pin permits the user to effect pure protrusive movement without side components.

Although the present invention has been described in connection with a particular embodiment, various modifications and variations also fall within the spirit of the present invention. Accordingly, it is intended that the scope of the present invention be measured only by the following claims and by their reasonable equivalents.

What is claimed is:

1. A dental articulator, comprising:
   a lower frame having a pair of condyles thereon defining a hinge axis;
   an upper frame carrying a pair of guides for slidably and pivotally receiving said condyles to permit the relative positions of said upper and lower frames to simulate movements of the human jaw;
   retainers laterally outboard of said condyles on opposite sides of said articulator connecting said upper frame to said lower frame, said retainers urging said guides into contact with said condyles while permitting the frames to be moved to simulate jaw movements, wherein said guides separate from said condyles when said upper frame is pivoted toward a fully open position, and said retainers including means functioning as a hinge on which said upper frame can pivot beyond the point where the condyles separate from the guides wherein said retainers intersect said hinge axis when said upper and lower frames are in centric relationship.

2. The articulator of claim 1 wherein said retainers urge said frames into centric relationship.

3. The articulator of claim 1, wherein said retainers intersect said hinge axis when said upper and lower frames are in centric relationship.

4. The articulator of claim 3, wherein said retainers include loops of elastomeric material having a generally circular cross section and wherein said upper frame can pivot on said hinge axis from a closed position through about 180° to a fully open position.

5. The articulator of claim 3, wherein said retainers include loops of elastomeric material and said upper frame can pivot on said hinge axis from a closed position through about 180° to a fully open position, and further comprising:
   a sleeve placed on the retainer so that a loop of said retainer extends from each end of said sleeve, said sleeve separating said upper frame from said lower frame when said articulator is pivoted to a fully open position.

6. The articulator of claim 5, further comprising coaxial pins inserted into said upper frame to which said retainers are attached, said pins lying along said hinge axis when said upper and lower frames are in centric relationship so that said retainers offer no elastic resistance to pivotal motion between said upper and lower frames when said frames are in centric relationship, but wherein said retainers offer elastic resistance to side shift and protrusive movement.

7. The articulator of claim 5, wherein said sleeve maintains said retainers on said upper and lower frames.

8. The articulator of claim 1, further comprising:
   an incisal pin on the upper frame extending generally vertically downward which is supported by the lower frame when the articulator is in a fully closed centric position; and
   a generally horizontal incisal locator rod laterally moveable into and out of contact with said incisal pin for locating said upper and lower frames in a non-centric relationship.

9. The articulator of claim 8, in which the articulator simulates protrusive jaw movement and wherein the locator rod extends forward alongside the incisal pin in the direction of protrusive movement.

10. A dental articulator, comprising:
    an upper frame and a lower frame;
    guide structure guiding relative movement of said frames to simulate movement of the human jaw including hinging movement;
    a retainer on either side of said articulator biasing said frames into engagement during the movements simulating movement of the human jaw, while permitting hinging movement into a fully open position of about 180° from a closed position, said retainer being constructed to maintain the frames separated from each other in moving from the position for simulating jaw movement to the fully open position, wherein said retainers comprise resilient elements having stiffened central sections that provide the frame separating function.

11. A dental articulator, comprising:
    a lower frame having a pair of condyles thereon defining a hinge axis;
    an upper frame carrying a pair of guides for slidably and pivotally receiving said condyles to permit the relative positions of said upper and lower frames to simulate movements of the lower jaw;
    a pair of resilient retainers adjacent to said condyles and said guides on opposite sides of said articulator connecting said upper frame to said lower frame, one end of each retainer connected to said upper frame and the other end, pivotally connected to said lower frame, said retainers urging said guides into contact with said condyles while permitting the frames to be moved to simulate jaw movements, wherein said guides separate from said condyles when said upper frame is pivoted toward a fully open position, and the ends of said retainers connected to said lower frame are means functioning as a hinge on which said upper frame can pivot beyond the point where the condyles separate from the guides.

12. The articulator of claim 11, wherein each of said retainers comprise a loop of elastomeric material and a sleeve positioned on the retainer in a manner such that said retainer extends from each end of said sleeve for connection to said frames.

* * * * *